United States Patent [19]

Turk et al.

[11] 4,215,995

[45] Aug. 5, 1980

[54] TEST MEANS AND ASSAY FOR DETERMINING THE UREA CONTENT OF FLUIDS

[75] Inventors: Richard S. Turk, Elkhart; Adam P. Zipp, Goshen, both of Ind.

[73] Assignee: Miles Laboratories, Inc., Elkhart, Ind.

[21] Appl. No.: 39,113

[22] Filed: May 15, 1979

Related U.S. Application Data

[63] Continuation-in-part of Ser. No. 915,587, Jun. 15, 1978, abandoned.

[51] Int. Cl.$^2$ ...................... G01N 31/22; G01N 33/16
[52] U.S. Cl. ................................. 23/230 R; 23/230 B; 23/924; 422/56
[58] Field of Search ................. 23/230 B, 230 R, 924; 422/56; 252/408

[56] References Cited

U.S. PATENT DOCUMENTS

| | | | |
|---|---|---|---|
| 3,092,463 | 6/1963 | Adams, Jr. et al. ................. | 422/56 |
| 3,212,855 | 10/1965 | Mast et al. ........................... | 422/56 |
| 3,449,080 | 6/1969 | Edwards ............................. | 422/56 X |
| 3,723,064 | 3/1973 | Liotta ................................. | 23/230 B X |
| 3,890,099 | 6/1975 | Wung ................................. | 23/230 B |
| 3,901,657 | 8/1975 | Lightfoot ........................... | 422/57 X |
| 4,061,468 | 12/1977 | Lange et al. ....................... | 23/230 B X |
| 4,074,972 | 2/1978 | Denney ............................. | 23/230 B |

*Primary Examiner*—Arnold Turk
*Attorney, Agent, or Firm*—Roger N. Coe

[57] ABSTRACT

Test means, method for making same and method for assaying the urea content of fluids such as blood serum, plasma, urine and spinal fluid are disclosed. The preferred method for making the test means involves a three stage application of reagents separated from each other on an acid modified carrier matrix. One reagent is o-phthalaldehyde and the other reagent is 3-hydroxy-1,2,3,4-tetrahydrobenzo[h] quinoline, 3-acetoxy-1,2,3,4-tetrahydrobenzo[h]quinoline or their dihydrochloride salts. Stability of the reagents is achieved and precipitation of serum proteins is avoided. Moreover, the interfering color due to the presence of bilirubin is minimized when the urea content of serum is determined.

12 Claims, No Drawings

TEST MEANS AND ASSAY FOR DETERMINING THE UREA CONTENT OF FLUIDS

CROSS REFERENCE TO RELATED APPLICATION

This application is a continuation-in-part of U.S. Ser. No. 915,587, filed June 15, 1978, now abandoned.

BACKGROUND OF THE INVENTION

1. Field of the Invention

This invention relates to assaying the urea content of fluids and aqueous solutions and, more particularly, to test means and methods for improving the stability of colorimetric assays for the rapid and accurate determination of urea.

2. Description of the Prior Art

Urea is a chief end product of protein metabolism in the human body. Urea concentration in the blood accordingly provides an indicator of kidney function. Elevation of the urea concentration in blood signifies inadequate kidney function. Since toxic substances are retained in the blood in rough proportion to urea level, a high nonprotein nitrogen or blood-urea-nitrogen level is a matter of concern to a physician.

One of the commonest causes of high blood urea values (uremia) is renal disease which may be either acute or chronic. Any of the inflammatory, degenerative, congenital or neoplastic ills that affect the kidney can cause uremia, and the degree of uremia provides a rough index to the severity of the existing condition.

In practice, the concentration of urea in blood is normally expressed in terms of blood-urea-nitrogen (BUN). This BUN value represents the amount of nitrogen present as urea and is approximately one half of the total urea value. When either the urea or nitrogen value has been determined, the other value can be calculated therefrom.

The normal range of BUN values in individuals varies from between 5 and 20 milligram percent (mg%). No significance is ordinarily attached to the lower values. However, elevations in BUN values generally indicate the presence of an abnormal condition. The most common cause of increased blood-urea-nitrogen is inadequate excretion, usually due to a kidney disease or urinary obstruction. For example, in acute nephritis the BUN level may vary from 25 mg% to as high as 160 mg%. Elevated urea retention also occurs in extensive parenchymatous destruction of kidney tissue, as in pyelonephritis, advanced nephrosclerosis, renal tuberculosis, renal cortical necrosis, renal malignancy, renal suppuration or chronic gout. Although BUN values can rise to as high as 400 mg%, they usually do not exceed 200 mg%. A need thus exists in the medical field today for a rapid and accurate analytical technique for determining BUN. In the past, cumbersome wet chemical methods have been used to perform such analysis. Other methods, such as conductivity methods, spectrophotometric techniques and colorimetric techniques have also been utilized. While these methods are generally accurate, the techniques tend to be somewhat time consuming and can require careful interpretation.

In perhaps the most commonly used method for determination of urea in biological fluids, urea is hydrolyzed to ammonium carbonate by means of the enzyme urease in the presence of a buffer solution. The amount of ammonia liberated is determined colorimetrically. This first method is very specific and sensitive, but has the drawback of urease inhibition and inactivation, the problem of reagent stability and a further drawback in that the method measures endogenous ammonia. Another procedure utilizes hydrolysis with urease and requires special apparatus not always available in the routine laboratory. Yet another procedure employs the direct colorimetric reaction of urea in a protein free filtrate with an organic reagent such as diacetyl monoxime. The diacetyl reaction has the disadvantage that the color produced in unstable, the fact that colors are developed at about 95° C. and that the volatile diacetyl has an odor which is unpleasant to at least some individuals.

In U.S. Pat. No. 4,074,972, assigned to American Monitor Corporation, a liquid assay for urea is disclosed which involves a reaction between a sample of biological fluid and an acidic reagent solution of o-phthalaldehyde and 8-(4-amino-1-methyl butyl amino)-6-methoxyquinoline. There is neither a teaching nor a suggestion of incorporating the reagent solution into a test means, such as a carrier matrix, let alone a strong cation exchange resin loaded carrier matrix which is in its acid form. Moreover, this patent does not disclose any method of overcoming the stability problem which occurs when the reagents of the acidic reagent solution are combined. Another problem of the disclosed assay is the fact that determinations must be made at wavelengths in the range of 470 to 540 nanometers which is close to the blank color absorption maximum resulting in the likelihood of reflectance spectroscopy measurement errors.

In the industrial area, urea is an important addition to process fluids such as plating baths, and a quick means to determine the concentration of urea therein is of great value. Urea itself is used as a fertilizer, and a quick means for assaying this material is important as a control measure in its production and use.

Accordingly, for both medical and industrial applications there is a need for assaying the urea content of fluids which can be run quickly without highly specialized equipment or trained technicians to operate such equipment.

SUMMARY OF THE INVENTION

An object of the present invention is to provide test means for determining the urea content of fluids wherein stability of reagents utilized to make the test means is achieved.

Another object of the present invention is to minimize interferences due to serum turbidity and the presence of bilirubin when assaying the urea content of blood serum.

Still another object of the present invention is to provide test means having high specificity and sensitivity for determining urea in fluids over a range of concentrations.

Yet another object of the present invention is to provide colorimetric test means capable of detecting urea when the quantity of fluid to be assayed is limited.

A further object of the present invention is to provide a BUN assay which can be run quickly without the need for highly specialized equipment.

In accordance with the present invention test means for detecting urea present in a test fluid comprises an acid modified carrier member incorporating reagents separated from each other. One reagent is o-phthalaldehyde, and the other reagent is 3-hydroxy-1,2,3,4-tetrahydrobenzo[h]quinoline, 3-acetoxy-1,2,3,4-tetrahydrobenzo[h]quinoline, or their dihydrochloride salts. Advantageously, the reagents are separated from each other by a polymeric material.

The test means can be used by momentarily dipping it into a test sample or otherwise introducing test sample onto the carrier matrix, and observing any detectable color change which results.

DESCRIPTION OF THE PREFERRED EMBODIMENTS

For the purposes of this application the term "fluids" shall be understood to refer to body fluids such as blood serum, blood plasma, urine, spinal fluid and, in addition, shall refer to aqueous solutions containing urea. Although the most preferred application of the test means and method of this invention is to body fluids, such as blood serum, it should be understood that the test means and method can be applied to industrial fluids as well.

In accordance with the present invention a unique reagent strip is prepared by incorporating with a carrier matrix the reagents herein described suitably separated thereon, e.g., by a polymeric barrier. The expression "carrier matrix" refers to bilbulous and nonbibulous matrices which are insoluble in and maintain their structural integrity when exposed to water or other physiological fluids. Suitable bibulous matrices which can be used include paper, cellulose, wood, synthetic resin fleeces, woven and nonwoven fabrics and the like. Nonbibulous matrices include glass fiber and organo-plastic materials, such as polypropylene and the like. The matrix can advantageously be affixed to an insoluble support member such as organo-plastic strip, e.g., polystyrene, by suitable means such as double faced adhesive tape, for ease of use.

The reagents incorporated with the carrier matrix react with urea under acid conditions to produce a chromogen which absorbs light above about 550 nanometers and normally between about 550 and about 700 nanometers. Quantitation can be achieved by monitoring the change in reflectance at about 620 nanometers after application of or contact with sample.

In order to achieve the desired acidity for the conditions of the assay, it has been found necessary to modify or impregnate the carrier matrix with an acid material. One method of preparing the acid modified carrier matrix involves impregnating the carrier matrix with acid materials such as benzenesulfonic acid, benzenedisulfonic acid, polystyrenesulfonic acid or the like in an amount between about 5 and about 10 gram percent.

An alternate method of preparing the acid modified carrier matrix involves loading the carrier matrix with strong cation exchange resins, preferably in their acid form. Ion exchange resin loaded carrier matrices containing Amberlite IR 120 (Rohm & Haas, Philadelphia, Pa.) or Dowex 50 (Dow Chemical Co., Midland, Mich.) are particularly preferred as sulfonic acid modified carrier materials, especially when serum is used. These particular ion exchange resins are sulfonic acid modified polystyrenes crosslinked with various amounts of divinylbenzene. Each carrier matrix is loaded with between about 25 and about 50 percent by weight of ion exchange resin and preferably between about 35 and about 50 percent by weight.

Two reagents are used to prepare the test means. One reagent is o-phthalaldehyde and the other reagent is 3-hydroxy-1,2,3,4-tetrahydrobenzo[h]quinoline, 3-acetoxy-1,2,3,4-tetrahydrobenzo[h]quinoline or their dihydrochloride salts. 3-hydroxy-1,2,3,4-tetrahydrobenzo[h] quinoline is preferred.

While in accordance with the present invention the reagents must be applied to the carrier matrix separately, the order of application of the reagents is immaterial. Thus, any reagent can be applied first. The sulfonic acid material can be applied to the carrier matrix either simultaneously with the first reagent or an ion exchange resin loaded carrier matrix can be used.

In the preferred method the first stage thus comprises application of at least one reagent to the carrier matrix. The second stage normally comprises applying polymer to the carrier matrix, the polymer being present in a solvent that does not dissolve either the first reagent or the sulfonic acid material. Polymers such as methylcellulose, cellulose acetate, polyethylene oxide, styrene-butadiene copolymer, styrene-isoprene copolymer, polystyrene and styrene-acrylonitrile copolymer can be used. Finally, the third or final stage comprises applying the other reagent to the carrier matrix, the reagent being present in a solvent which does not dissolved the polymeric material applied in the second stage. Normally, the reagent strip is permitted to dry between each stage.

Suitable solvents for use with o-phthalaldehyde include water, methanol, acetone and hexane. Water, methanol or a mixture thereof is the preferred solvent if the reagent o-phthalaldehyde is applied in the first stage. Acetone or hexane is the preferred solvent if the reagent o-phthalaldehyde is applied in the third stage. With respect to the polymers suitable solvents include chloroform, acetone, benzene, toluene and the like. Suitable solvents for the other reagent include water, methanol, and methanol and acetone mixtures. Water is again the preferred solvent when the reagent is applied in the first stage and either methanol or a methanol-acetone mixture is the preferred solvent when the reagent is applied in the third stage.

The reagents can be used in various concentrations. Normally, o-phthalaldehyde is present in the amount of from about 300 milligram percent (mg%) to 800 mg% and preferably is present in an amount between about 500 mg% and 600 mg%. The other reagent is normally present in an amount between about 200 mg% and about 500 mg% when a dihydrochloride salt is employed and in the amount of from about 600 mg% to about 1200 mg% when the free base is used. The concentrations of the polymeric material are not critical provided an amount between about 0.5 gram percent (g%) and about 5 g% is used. Preferably, the polymeric material should be present in an amount between about 1 g% and 3 g%.

While the preferred method of preparing the test means is by three stage impregnation followed by drying, the test means of the present invention can also be made by other suitable techniques, such as printing on one or more sides of a matrix or suitably applying separate reagents to opposite sides of a substrate or matrix.

Test means according to the present invention is advantageously used by momentarily dipping it in a test sample or by otherwise introducing a test sample onto the carrier matrix, and observing any detectable color change which results.

EXAMPLE 1

The preparation of test means in the form of a test device will not be described. Hydrochloric acid (10–20%) prewashed cation exchange loaded filter paper, SA-2, obtained from Reeve Angel, Clifton, N.J., having an exchange capacity of about 4 milliequivalents per gram of dry resin was impregnated with the following solutions in three stages after being rinsed with dionized water and dried. The SAZ paper is a paper containing Amberlite IR120 ion exchange resin sulfonated to give ion exchange properties. The resin is supplied in the sodium form and the paper contains between 45 and 50 percent of resin.

FIRST IMPREGNATION STAGE

The filter paper was impregnated by dipping into a solution containing the following materials in the amounts indicated.

| Material | Amount |
| --- | --- |
| water | 100 milliliters (ml) |
| maleic anhydride-methyl vinyl ether copolymer (stabilizer) | 100 milligrams (mg) |
| boric acid (color stabilizer) | 2.5 grams (g) |
| o-phthalaldehyde | 300 mg |
| 7 (2,3-dihydroxypropyl)-theophylline (stabilizer) | 10 g |

Following impregnation, the paper was dried at 60° C. for 30 minutes.

SECOND IMPREGNATION STAGE

The dried impregnated paper from the first stage was then impregnated by dipping into a solution containing the following materials in the amounts indicated:

| Material | Amount |
| --- | --- |
| toluene | 100 ml |
| polystyrene pellets (Styron, Dow Chemical Co., Midland, Mich.) | 2 g |

THIRD IMPREGNATION STAGE

The dried impregnated paper from the second stage was then impregnated by dipping into a solution containing the following materials in the amounts indicated. Materials (1) and (4) were dissolved first, materials (2) and (3) were separately dissolved and then added to materials (1) and (4) to form the solution.

| Material | Amount |
| --- | --- |
| (1) methanol | 30 ml |
| (2) acetone | 70 ml |
| (3) hydroxypropyl celluose (Stabilizer) | 0.5 g |
| (4) 3-hydroxy-1,2,3,4-tetrahydro-benzo[h]quinoline hydrochloride | 300 mg |

The paper was then dried at 60° C. for 10 minutes and applied to a polystyrene substrate by means of double faced adhesive tape. The polystyrene substrate provides a suitable handle with which to dip the resulting reagent impregnated paper test device into a solution for purposes of assaying the urea content of the solution.

The color intensity of urea nitrogen reagent strips to various urea concentrations is shown in the following table.

One part of a serum sample containing the indicated amount of urea nitrogen is diluted with two parts of water and 0.030 ml are applied to the surface of a test device prepared as in Example I. After incubating at 37° C. for one minute, the reflectance of the reagent strip is measured at 620 nanometers (nm) relative to a barium sulfate, white reflecting surface.

Table 1

| Urea Nitrogen Concentration mg % | Reflectance % | Urea Nitrogen Concentration mg % | Reflectance % |
| --- | --- | --- | --- |
| 0 | 75 | 50 | 30 |
| 5 | 62 | 60 | 27 |
| 10 | 54 | 70 | 25 |
| 20 | 44 | 90 | 21 |
| 30 | 38 | 120 | 18 |
| 40 | 33 | 150 | 15 |

EXAMPLE II

The preparation of another test means will now be described. Filter paper loaded at 40% by weight with Dowex 50W, supplied in its acid form, 8% crosslinked with divinylbenzene (Dow Chemical Co., Midland, Mich.) was impregnated with the following solutions in three stages.

FIRST IMPREGNATION STAGE

The filter paper was impregnated by dipping into a solution containing the following materials in the amounts indicated.

| Material | Amount |
| --- | --- |
| water | 100 milliliters (ml) |
| polyethylene oxide | 50 milligrams (mg) |
| o-phthalaldehyde | 300 mg |
| 7-(2,3-dihydroxypropyl)-theophylline (stabilizer) | 10 g |
| boric acid | 2.5 g |

Following impregnation, the paper was dried at 60° C. for 30 minutes.

SECOND IMPREGNATION STAGE

The dried impregnated paper from the first stage was then impregnated by dipping into a solution contain the following materials in the amounts indicated:

| Material | Amount |
| --- | --- |
| toluene | 100 ml |
| styrene-acrylonitrile copolymer | 2 g |

Following impregnation with the styrene copolymer, the paper was dried at 60° C. for 15 minutes.

THIRD IMPREGNATION STAGE

The dried impregnated paper from the second stage was then impregnated by dipping into a solution containing the following materials in the amounts indicated. Materials (1) and (4) were dissolved first; materials (2) and (3) were separately dissolved and then added to materials (1) and (4) to form the solution.

| Material | Amount |
| --- | --- |
| (1) methanol | 30 ml |
| (2) acetone | 70 ml |
| (3) hydroxypropyl cellulose | 0.5 g |
| (4) 3-acetoxy-1,2,3,4-tetrahydro- | 300 mg |

-continued

| Material | Amount |
|---|---|
| benzo[h]quinoline hydrochloride | |

The paper was then dried at 60° C. for 10 minutes and applied to a polystyrene substrate by means of double faced adhesive tape. The polystyrene substrate provides a suitable handle with which to dip the resulting reagent impregnated paper test device into a solution for purposes of assaying the urea content of the solution.

Other test means were prepared by the same procedure of this Example II using Dowex 50W which was 2% crosslinked with divinylbenzene and 16% crosslinked with divinylbenzene. It was found that intensity of color production dipped in a sample of urea could be controlled by varying the amount of crosslinking. Intensity varied inversely with the degree of crosslinking.

The rate of color formation of urea nitrogen reagent strips prepared with carries containing ion exchange resins of varied divinylbenzene (DVB) crosslinking is shown in the following table.

Reagent strips were prepared as in Example II with ion exchange resin loaded paper containing Dowex 50 resins of 2%, 8% and 16% divinylbenzene crosslinking. Urea samples were then diluted, incubated for one minute at 37° C. and measured on a reflectometer as in Table 1.

Table 2
Reflectance Readings at Various Urea Concentrations and DVB Crosslinking
(Reflectance readings and color intensity vary inversely)

| Urea Nitrogen Concentration | % DVB Crosslinking | | |
|---|---|---|---|
| mg % | 2 | 8 | 16 |
| 20 | 37 | 44 | 66 |
| 40 | 27 | 33 | 56 |
| 60 | 21 | 27 | 50 |

The rate of color formation of urea nitrogen reagent strips prepared with carries loaded having varied amounts of ion exchange resin is illustrated in the following table.

Reagent strips were prepared as in Example I with ion exchange resin loaded paper containing 25%, 35% and 50% by weight of an 8% divinylbenzene crosslinked ion exchange resin. Urea samples were diluted, incubated for one minute at 37° C. and measured on a reflectometer as in Table. 1.

Table 3
Reflectance Readings at Various Urea Concentration and Resin Loadings

| mg % Urea Nitrogen Concentration | % Resin Loading | | |
|---|---|---|---|
| | 25 | 35 | 50 |
| 20 | 58 | 51 | 44 |
| 40 | 48 | 40 | 33 |
| 60 | 42 | 33 | 27 |

EXAMPLE III

Using ion exchange paper as described in Example II a test device was prepared by the following three stage procedure:

FIRST IMPREGNATION STAGE

The paper was impregnated by dipping into a solution containing the following materials in the amounts indicated.

| Materials | Amount |
|---|---|
| water | 25 ml |
| polyethylene oxide | 100 mg |
| 7-(2,3 dihydroxypropyl)-theophylline | 10 g |
| ethylenedinitrilotetra-acetic acid, dipotassium salt | 1.5 g |
| sodium lauryl sulfate | 100 mg |
| methanol | 75 ml |
| glycerol | 0.2 ml |
| boric acid | 4.5 g |
| o-phthalaldehyde | 600 mg |

Following impregnation the paper was dried at 50° C. for 20 minutes.

SECOND IMPREGNATION STAGE

| Materials | Amount |
|---|---|
| toluene | 100 ml |
| polystyrene pellets | 3 g |

Following impregnation with the styrene polymer the paper was dried at 50° C. for 10 minutes.

THIRD IMPREGNATION STAGE

The dried impregnated paper from the second stage was then impregnated by dipping into a solution containing the following materials in the amounts indicated. Materials (2), (3), and (4) were separately combined and then material (1) was added to form the solution.

| Materials | Amount |
|---|---|
| (1) methanol | 25 ml |
| (2) acetone | 75 ml |
| (3) hydroxypropyl cellulose | 0.75 g |
| (4) 3-hydroxy-1,2,3,4-tetra-hydrobenzo[h] quinoline | 900 mg |

The paper was dried for 5 minutes at 50° C. The resulting test device can be used with blood serum or plasma which has not been diluted, as required in the case of the test device of Examples I and II, for concentrations up to 70 mg% urea nitrogen.

It will also be understood that the use of the stabilizer hydroxypropyl cellulose is not critical to the present invention. It will be further understood that a stabilizer such as caffeine can be substituted for dyphylline employed in the following example. It has been found that dyphylline or its substitute should be used in an amount greater than 5 gram percent.

EXAMPLE IV

For comparison purposes, another test device is prepared by the following procedure.

FIRST STAGE

Whatman 3MM filter paper is acid modified by dipping it into a solution containing the following materials in the amounts indicated.

| Material | Amount |
| --- | --- |
| water | 100 ml |
| benzenedisulfonic acid | 10 g |
| N-naphthylethylenediamine dihydrochloride | 400 mg |
| dyphylline | 10 g |
| maleic anhydride-methyl vinyl ether copolymer (stabilizer) | 0.1 g |

Following impregnation the paper is dried at 60° C. for 20 minutes.

SECOND STAGE

The dried impregnated paper from the first stage is then impregnated by dipping into a solution containing the following materials in the amounts indicated:

| Material | Amount |
| --- | --- |
| polyethlene oxide | 1 g |
| chloroform | 70 ml |
| acetone | 30 ml |

The paper is then dried at 60° C. for 20 minutes.

THIRD STAGE

The dried impregnated paper from the second stage is then impregnated by dipping into a solution containing the following materials in the amounts indicated:

| Material | Amount |
| --- | --- |
| hexane | 100 ml |
| o-phthalaldehyde | 300 mg |

The paper is then dried as before at 60° C. for 20 minutes. The resulting dried impregnated paper is then applied to a polystyrene substrate using double faced adhesive tape. The resulting reagent strip can be used to quantitate deproteinized samples. Undesirable precipitation occurs when attempts are made to quantitate samples containing protein. This fact emphasizes the significance of the discovery which has been made.

From the foregoing, it will be seen that this invention is well adapted to attain all of the ends and objects hereinabove set forth, together with other advantages which are obvious and which are inherent to the system. Three specific problems are solved by the preparation of reagent strips according to the present invention.

First, under the usual acid conditions of the assay serum proteins normally precipitate and interfere with the development of chromogen. The present invention eliminates the precipitation of serum proteins while providing a suitable acid matrix by using a strong cation exchange loaded paper.

Secondly, the reagents utilized are normally unstable. The present invention provides a method for incorporating the reagents on a paper matrix in a format such that the reagents are stabilized.

The third problem solved in accordance with the present invention is the minimization of error in reflectance spectroscopy measurements when determining the urea content of blood serum. The present invention utilizes a coupling agent which produces a chromogen detectable at wavelengths well above 550 nanometers, thereby overcoming the problem caused by a yellow blank reaction occurring on the strips and the interfering color caused by bilirubin and/or turbidity in serum, observed by absorption or reflectance spectroscopy. The use of 3-hydroxy-1,2,3,4-tetrahydrobenzo [h]quinoline or its dihydrochloride salt minimizes the blank reaction which occurs. In contrast, when primaquine diphosphate [8-(4-amino-1methylbutylamino)-6-methoxyquinoline]or N-naphthylethylenediamine dihydrochloride is used the chromogen produced develops color which must be measured at wavelengths near the absorption maximum of the blank reaction. Therefore, use of 3-hydroxy-1,2,3,4-tetrahydrobenzo[h] quinoline or its dihydrochloride salt allows measurements to be made at wavelengths where color, due to the blank reaction, is minimal.

Moreover, the present invention incorporates all reagents into a single matrix without the use of corrosive liquid reagents.

Although the present invention has great importance in the early detection of physiological disorders by determining the urea content of body fluids, as indicated herein it also has important application in the accurate determination of urea in industrial process fluids where urea concentration must be controlled within defined limits. Means for the determination of urea fluids, whether industrial or physiological, is of greatest value if the test means is conveniently rapid, reliable and simple enough for the technician to learn with ease. Moreover, in the case of medical diagnosis, the test means must be accurate enough to reflect variations in a subjects condition. These objectives are achieved using the present invention.

Obviously, many other modifications and variations of the invention as hereinabove set forth may be made without departing from the spirit and scope thereof.

What is claimed is:

1. Test means for detecting urea which comprises a strong cation exchange resin loaded carrier matrix which is in its acid form having incorporated therewith in separated relation the reagent o-phthalaldehyde and a reagent from the group consisting of 3-hydroxy-1,2,3,4-tetrahydrobenzo[h] quinoline, 3-acetoxy-1,2,3,4-tetrahydrobenzo[h]quinoline and their dihydrochloride salts.

2. The test means of claim 1 in which 3-acetoxy-1,2,3,4-tetrahydrobenzo[h]quinoline is present.

3. The test means of claim 1 in which 3-hydroxy-1,2 3,4-tetrahydrobenzo[h]quinoline is present.

4. The test means of claims 2 or 3 in which the reagent o-phthalaldehyde is present in an amount of from about 300 milligram percent to about 800 milligram percent and the other reagent is present in an amount of from about 200 milligram percent to about 500 milligram percent when dihydrochloride salt is used and in an amount of from about 600 milligram percent to about 1200 milligram percent when free base is used.

5. The test means of claim 1 in which the reagents are separated from each other by a polymeric material.

6. The test means of claim 1 wherein the carrier matrix is bibulous cellulose paper matrix.

7. The test means of claim 6 in which the carrier matrix is loaded with from about 25 to about 50 percent by weight of ion exchange resin.

8. The test means of claim 7 wherein the ion exchange resin is a resin having between about 2 and about 16 percent divinylbenzene crosslinking.

9. A method for detecting urea in a liquid test sample which comprises momentarily dipping the test means of claim 1 in the test sample and observing any detectable color change with results.

10. The method of claim 9 in which the test sample is blood serum.

11. The method of claim 9 in which the color change is observed by monitoring a change in reflectance above about 550 nanometers.

12. A method of preparing test means for assaying the urea content of fluids, which method comprises incorporating with a strong cation exchange resin loaded carrier matrix which is in its acid form first and second reagents separated from each other by a polymeric material, said first reagent comprising o-phthalaldehyde, and said second reagent comprising 3-hydroxy-1,2,3,4-tetrahydrobenzo[h]quinoline, 3-acetoxy-1,2,3,4-tetrahydrobenzo[h]quinoline, or their dihydrochloride salts.

* * * * *